US010420756B2

(12) United States Patent
Iversen et al.

(10) Patent No.: US 10,420,756 B2
(45) Date of Patent: Sep. 24, 2019

(54) METHODS AND COMPOSITIONS TO INHIBIT SYMPTOMS ASSOCIATED WITH VEISALGIA

(71) Applicants: Jacqueline M. Iversen, Lloyd Harbor, NY (US); James M. Iversen, Lloyd Harbor, NY (US)

(72) Inventors: Jacqueline M. Iversen, Lloyd Harbor, NY (US); James M. Iversen, Lloyd Harbor, NY (US)

(73) Assignee: SEN-JAM PHARMACEUTICAL LLC., Huntington, NY (US)

( * ) Notice: Subject to any disclaimer, the term of this patent is extended or adjusted under 35 U.S.C. 154(b) by 145 days.

(21) Appl. No.: 15/074,524

(22) Filed: Mar. 18, 2016

(65) Prior Publication Data

US 2016/0279112 A1    Sep. 29, 2016

Related U.S. Application Data

(60) Provisional application No. 62/138,665, filed on Mar. 26, 2015.

(51) Int. Cl.
| | |
|---|---|
| *A61K 31/192* | (2006.01) |
| *A61K 31/445* | (2006.01) |
| *A61K 9/00* | (2006.01) |
| *A61K 45/06* | (2006.01) |
| *A61K 31/196* | (2006.01) |
| *A61K 31/407* | (2006.01) |
| *A61K 31/4545* | (2006.01) |
| *A61K 31/495* | (2006.01) |
| *A61K 31/60* | (2006.01) |
| *A61K 31/603* | (2006.01) |

(52) U.S. Cl.
CPC .......... *A61K 31/445* (2013.01); *A61K 9/0056* (2013.01); *A61K 31/192* (2013.01); *A61K 31/196* (2013.01); *A61K 31/407* (2013.01); *A61K 31/4545* (2013.01); *A61K 31/495* (2013.01); *A61K 31/60* (2013.01); *A61K 31/603* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 4,496,548 | A * | 1/1985 | Moldowan | A61K 31/70 514/27 |
| 4,975,426 | A | 12/1990 | Sunshine et al. | |
| 5,053,396 | A * | 10/1991 | Blass | A61K 31/455 514/45 |
| 6,077,539 | A * | 6/2000 | Plachetka | A61K 9/0007 424/468 |
| 6,093,743 | A | 7/2000 | Lai et al. | |
| 6,274,627 | B1 | 8/2001 | Lai et al. | |
| 6,316,502 | B1 | 11/2001 | Lai et al. | |
| 6,589,991 | B1 | 7/2003 | Lai et al. | |
| 8,207,316 | B1 | 6/2012 | Bentwich | |
| 8,697,361 | B2 | 4/2014 | Johnson | |
| 2002/0022057 | A1 | 2/2002 | Battey et al. | |
| 2002/0151540 | A1 | 10/2002 | Lai et al. | |
| 2003/0181495 | A1 | 9/2003 | Lai et al. | |
| 2003/0187021 | A1 | 10/2003 | Edgar et al. | |
| 2004/0029927 | A1 | 2/2004 | Sunderraj et al. | |
| 2004/0142972 | A1 | 7/2004 | Edgar et al. | |
| 2004/0253311 | A1 * | 12/2004 | Berlin | A61K 9/209 424/472 |
| 2005/0009730 | A1 | 1/2005 | Edgar et al. | |
| 2005/0203105 | A1 * | 9/2005 | Tan | A61K 31/10 514/255.04 |
| 2005/0281751 | A1 | 12/2005 | Levin | |
| 2006/0009465 | A1 | 1/2006 | Edgar et al. | |
| 2006/0063754 | A1 | 3/2006 | Edgar et al. | |
| 2006/0063755 | A1 | 3/2006 | Edgar et al. | |
| 2006/0063928 | A1 | 3/2006 | Edgar et al. | |
| 2006/0094705 | A1 | 5/2006 | Edgar et al. | |
| 2007/0026051 | A1 | 2/2007 | Sunderraj et al. | |
| 2007/0086974 | A1 * | 4/2007 | Gawande | A61K 9/0056 424/78.15 |
| 2007/0093520 | A1 | 4/2007 | Caras | |
| 2007/0123571 | A1 | 5/2007 | Raj et al. | |
| 2007/0224128 | A1 | 9/2007 | Dennis et al. | |

(Continued)

FOREIGN PATENT DOCUMENTS

| | | |
|---|---|---|
| GB | 2435418 A | 8/2007 |
| WO | 1996032933 | 10/1996 |

(Continued)

OTHER PUBLICATIONS

Vane et al., The mechanism of action of aspirin, Thromb Res. Jun. 15, 2003;110(5-6):255-8, printed from https://www.ncbi.nlm.nih.gov/pubmed/14592543, 1 page, Abstract only.*
In the Know Zone, Blood Alcohol Concentration, Jan. 8, 2012, printed from https://web.archive.org/web/20120108165248/http://www.intheknowzone.com/substance-abuse-topics/binge-drinking/blood-alcohol-concentration.html, 4 pages.*
Tan, et al., "Suppression of alcohol-induced flushing by a combination of H1 and H2 histamine antagonists," British Journal of Dermatology (1982) 107, 647-652.
PCT International Search Report and Written Opinion for PCT/US16/23200 dated Mar. 18, 2016.

(Continued)

*Primary Examiner* — Gigi G Huang
(74) *Attorney, Agent, or Firm* — Hoffmann and Baron, LLP

(57) ABSTRACT

The present invention relates to a method of reducing or preventing the symptoms associated with the intake of alcohol. The method comprises administering to a subject an effective amount of a pharmaceutical composition prior to alcohol intake. The pharmaceutical composition comprises a non-steroidal anti-inflammatory drug and a $H_1$-antihistamine.

15 Claims, No Drawings

(56) References Cited

U.S. PATENT DOCUMENTS

| | | |
|---|---|---|
| 2007/0292498 A1 | 12/2007 | Hall et al. |
| 2008/0021083 A1 | 1/2008 | Daley |
| 2008/0131532 A1 | 6/2008 | Leitman et al. |
| 2008/0279786 A1 | 11/2008 | Cash |
| 2009/0156982 A1 | 6/2009 | Petrie et al. |
| 2009/0186872 A1 | 7/2009 | Edgar et al. |
| 2009/0258869 A1 | 10/2009 | Ron et al. |
| 2010/0041689 A1 | 2/2010 | Johnson et al. |
| 2010/0076006 A1 | 3/2010 | Johnson et al. |
| 2011/0053999 A1 | 3/2011 | Daley et al. |
| 2011/0065628 A1 | 3/2011 | Johnson et al. |
| 2011/0065659 A1* | 3/2011 | Daley .................. A61K 31/198 514/26 |
| 2011/0112159 A1 | 5/2011 | Johnson |
| 2011/0184039 A1 | 7/2011 | Mooney et al. |
| 2012/0172429 A1 | 7/2012 | Woolf et al. |
| 2012/0294802 A1 | 11/2012 | Russo et al. |
| 2012/0302592 A1 | 11/2012 | Johnson et al. |
| 2013/0029970 A1 | 1/2013 | Sprott et al. |
| 2013/0109674 A1 | 5/2013 | Leighton et al. |
| 2013/0109721 A1 | 5/2013 | Sprott et al. |
| 2013/0150419 A1 | 6/2013 | Daley et al. |
| 2013/0178453 A1 | 7/2013 | Rohde et al. |
| 2013/0189354 A1 | 7/2013 | Singh |
| 2013/0196960 A1 | 8/2013 | Rohde et al. |
| 2013/0337096 A1 | 12/2013 | Purcell |
| 2014/0050702 A1 | 2/2014 | Smith et al. |
| 2014/0155450 A1 | 6/2014 | Daley et al. |
| 2014/0206734 A1 | 7/2014 | Johnson |
| 2015/0132410 A1* | 5/2015 | Jacobs .................. A61K 31/495 424/692 |

FOREIGN PATENT DOCUMENTS

| | | |
|---|---|---|
| WO | 2006064747 A1 | 6/2006 |
| WO | 2006087968 A1 | 8/2006 |
| WO | 2006018997 A1 | 2/2007 |
| WO | 2007092333 A1 | 8/2007 |
| WO | 2007092334 A1 | 8/2007 |
| WO | 2009052421 A1 | 4/2009 |
| WO | 2012088431 A1 | 6/2012 |
| WO | 2012088469 A1 | 6/2012 |

OTHER PUBLICATIONS

Joris C. Verster, "The alcohol hangover—a puzzling phenomenon," Alcohol and Alcoholism, DOI:http://dx.doi.org/10.1093/alcalc/agm163:124-126 (Jan. 2008).

Rohsenow et al., "The role of beverage congeners in hangover and other residual effects of alcohol intoxication: a review," Curr Drug Abuse Rev., 3(2):76-9 (Jun. 2010) (abstract).

Pittler et al., "Interventions for Preventing or Treating Alcohol Hangover: Systemic Review of Randomised Controlled Trials," BMJ 331(7531):1515-1518 (Dec. 24, 2005).

Joseph Stromberg, "Your Complete Guide to the Science of Hangovers," Smitsonian.com, http://www.smithsonianmag.com/science-nature/your-complete-guide-to-the-science-of-ha . . . , pp. 1-6, Mar. 23, 2015.

Kim et al., "Effects of alcohol hangover on cytokine production in healthy subjects," Alcohol 31:167-170 (2003).

"HAMS: Harm Reduction for Alcohol, Can You Prevent a Hangover"? http://www.hamsnetwork.org/preventhangover/, pp. 1-4, Dec. 8, 2014.

\* cited by examiner

METHODS AND COMPOSITIONS TO INHIBIT SYMPTOMS ASSOCIATED WITH VEISALGIA

This application claims the benefit of U.S. Provisional Application Ser. No. 61/138,665, filed Mar. 26, 2015, which is incorporated herein by reference in its entirety.

FIELD OF THE INVENTION

The present invention relates to methods, and compositions, for reducing/preventing the acute symptoms associated with the moderate or excessive intake of alcohols, particularly ethanol in the form of alcoholic beverages.

BACKGROUND OF THE INVENTION

The symptoms caused by the moderate or excessive (i.e., intoxicating) intake of alcohol are unpleasant, particularly in the post-exhilaration or veisalgia stage (i.e., "hangover"). Such symptoms include, for example, substantial physical and mental fatigue, nausea, loss of appetite, tremors of the hand and limbs (the "shakes"), joint weakness/pain, dehydration, irritability, lack of coordination, concentration difficulties, sleeplessness, impaired memory and visual-spatial skills, headache, drowsiness, dry mouth, dizziness, gastrointestinal complaints, sweating, and anxiety.

Excessive drinking is defined as four or more drinks per occasion for women; five or more drinks per occasion for men; high weekly use; and any alcohol use by pregnant women or those under age 21. Excessive drinking typically is associated with attaining blood alcohol content (BAC) of 0.055% and above.

However, even moderate drinking causes substantial hangover symptoms in some people. Moderate drinking is defined as: no more than 3-4 standard drinks per drinking episode; no more than 9 drinks per week for women and 12-14 for men; and limiting rate of drinking to keep BAC below 0.055%.

Interestingly, hangover symptoms develop when BAC returns to zero. It is not known why these symptoms are present after alcohol and its metabolites are eliminated from the body. ("The alcohol hangover—a puzzling phenomenon," Joris C. Verster, *Alcohol and Alcoholism*, DOI:http://dx.doi.org/10.1093/alcalc/agm163; 124-126 (January 2008))

Additionally, congeners, i.e., trace chemicals produced during fermentation contained in some beverages, contribute to hangover symptoms. Studies have shown that high-congener, darker-colored liquors like bourbon and whiskey result in more severe hangover symptoms than lighter-colored or clear liquors like vodka, which has none. ("The role of beverage congeners in hangover and other residual effects of alcohol intoxication: a review," Rohsenow et al., *Curr Drug Abuse Rev.*, 3(2):76-9 (June 2010).) It has been suggested that one particular congener, methanol, perhaps accounts for the enduring effects of hangover symptoms.

According to 2011 and 2013 studies published in the *American Journal of Preventive Medicine*, excessive drinking and resulting hangovers cost the American economy more than $223 billion nationally. The Center for Disease Control and Prevention (which studies the negative externalities of alcohol consumption each decade) estimates that over seventy percent of such costs come from lost workplace productivity, which suggests that the economic drag from hangovers is about $160 billion.

For such reasons, a search for remedies for hangover symptoms has persisted. A 2005 study assessed the clinical evidence for the effectiveness of medical interventions for preventing or treating alcohol hangover ("Interventions for Preventing or Treating Alcohol Hangover. Systemic Review of Randomised Controlled Trials," Pittler et al., *BMJ* 331 (7531):1515-1518 (2005 Dec. 24)). In particular, eight randomized controlled trials assessing eight different interventions were reviewed. The agents tested were propranolol, tropisetron, tolfenamic acid, fructose or glucose, and the dietary supplements *Borago officinalis* (borage), *Cynara scolymus* (artichoke), *Opuntia ficus-indica* (prickly pear), and a yeast based preparation. Significant intergroup differences for overall symptom scores and individual symptoms were reported only for tolfenamic acid, γ linolenic acid from *B officinalis*, and a yeast based preparation. It was concluded that "No compelling evidence exists to suggest that any conventional or complementary intervention is effective for preventing or treating alcohol hangover."

Clearly, there is a need for a more effective and accessible manner by which to manage the symptoms of veisalgia.

SUMMARY OF THE INVENTION

In one aspect, the present invention provides a method of inhibiting the symptoms associated with intake of alcohol. The method comprises administering to a subject an effective amount of a pharmaceutical composition prior to alcohol intake. The pharmaceutical composition comprises a) a non-steroidal anti-inflammatory drug, and/or a salt thereof; and b) an $H_1$-antihistamine, typically a non-sedating $H_1$-antihistamine. Typically, the symptoms include fatigue and/or headache and/or thirst.

Typically, the alcohol is ethanol in the form of beverages. Typically, the excessive intake of alcohol is an amount which provides a blood alcohol concentration of up to about 0.17%. Typically, the pharmaceutical composition is administered at most 60 minutes before intake of alcohol, or at most 5 minutes before intake of alcohol.

Typically, the non-steroidal anti-inflammatory drug is aspirin, ibuprofen, naproxen, diclofenac, diflunisal, etodolac, indomethacin, ketoprofen, ketorolac, meloxicam, nabumetone, oxaprozin, piroxicam, salsalate, sulindac, tolmetin or combinations thereof. Typically, the $H_1$-antihistamine is fexofenadine, loratadine, cetirizine, desloratadine or combinations thereof.

In a preferred embodiment, the non-steroidal anti-inflammatory drug is naproxen sodium and the $H_1$-antihistamine is fexofenadine. In one embodiment, the amount of naproxen sodium is about 220 mg to about 880 mg, and the amount of fexofenadine is about 60 mg to about 120 mg. In one embodiment, the naproxen sodium and the fexofenadine is combined in one unit dose. In one embodiment, the naproxen sodium and the fexofenadine is in the form of a tablet, lozenge or chewing gum.

In one embodiment, the amount of ibuprofen is about 200 mg to about 800 mg. In one embodiment, the amount of aspirin is about 325 mg to about 1000 mg. In one embodiment, the amount of loratadine is about 10 mg to about 20 mg. In one embodiment, the amount of cetirizine is about 5 mg to about 20 mg. In one embodiment, the amount of desloratidine is about 5 mg to about 10 mg.

In one aspect, the present invention provides a method of inhibiting the symptoms associated with intake of alcohol, comprising administering to a subject an effective amount of a pharmaceutical composition prior to alcohol intake, wherein the pharmaceutical composition consists essentially of about 220 mg to about 880 mg of naproxen sodium, and about 60 mg to about 120 mg fexofenadine.

In one aspect, the present invention provides a pharmaceutical composition comprising a) a non-steroidal anti-inflammatory drug, and/or a salt thereof; and b) a non-sedating $H_1$-antihistamine. In one embodiment, the pharmaceutical composition is in the form of an orally-dissolving tablet or lozenge.

In one embodiment, the pharmaceutical composition comprises the non-steroidal anti-inflammatory drug of aspirin, ibuprofen, naproxen, diclofenac, diflunisal, etodolac, indomethacin, ketoprofen, ketorolac, meloxicam, nabumetone, oxaprozin, piroxicam, salsalate, sulindac, tolmetin or combinations thereof.

In one embodiment, the pharmaceutical composition comprises the non-sedating $H_1$-antihistamine of fexofenadine, loratadine, cetirizine, desloratadine, or combinations thereof.

In one embodiment, the pharmaceutical composition comprises naproxen sodium and fexofenadine. Typically, the amount of naproxen sodium is about 110 mg to about 900 mg, and the amount of fexofenadine is about 25 mg to about 200 mg. In one embodiment, the amount of naproxen sodium is about 220 and the amount of fexofenadine is about 60 mg. In one embodiment, the naproxen sodium and the fexofenadine is in the form of an orally-dissolving tablet or lozenge combined in a one unit dose.

In one embodiment, the pharmaceutical composition comprises ibuprofen in the amount of about 200 mg to about 800 mg. In one embodiment, the pharmaceutical composition comprises aspirin in the amount of about 325 mg to about 1000 mg. In one embodiment, the pharmaceutical composition comprises loratadine in the amount of about 10 mg to about 20 mg. In one embodiment, the pharmaceutical composition comprises cetirizine in the amount of about 5 mg to about 20 mg. In one embodiment, the pharmaceutical composition comprises desloratidine in the amount of about 5 mg to about 10 mg.

DETAILED DESCRIPTION OF THE INVENTION

The present invention is directed to methods, and pharmaceutical compositions, to reduce and/or prevent the symptoms associated with moderate and excessive intake of alcohol. The methods include the administration of particular pharmaceutical compositions before the onset of such symptoms.

Throughout this specification, quantities are defined by ranges, and by lower and upper boundaries of ranges. Each lower boundary can be combined with each upper boundary to define a range. The lower and upper boundaries should each be taken as a separate element.

The pharmaceutical composition comprises a) at least one non-steroidal anti-inflammatory drug ("NSAID"), and/or salts thereof, and b) at least one antihistamine of the non-sedating H1 antagonist group ("$H_1$-antihistamines").

The NSAID of the present invention includes any NSAID. Examples of suitable NSAIDs include, but are not limited to, aspirin (i.e., acetylsalicylic acid); ibuprofen (i.e., isobutylphenylpropanoic acid); naproxen (i.e., 6-methoxy-α-methyl-2-naphthaleneacetic acid); diclofenac (i.e., 2-[(2,6-dichlorophenyl)-amino]benzene acetic acid); diflunisal (i.e., 2',4'-difluoro-4-hydroxybiphenyl-3-carboxylic acid); etodolac (i.e., (RS)-2-(1,8-Diethyl-4,9-dihydro-3H-pyrano [3,4-b]indol-1-yl)acetic acid); indomethacin (i.e., 2-{1-[(4-Chlorophenyl)-carbonyl]-5-methoxy-2-methyl-1H-indol-3-yl}acetic acid); ketoprofen (i.e., 3-benzoyl-α-methyl-benzeneacetic acid); ketorolac (i.e., 2-amino-2-(hydroxymethyl)-1,3-propanediol); meloxicam (i.e., 4-hydroxy-2-methyl-N-(5-methyl-2-thiazolyl)-2H-1,2-benzothiazine-3-carboxamide-1,1-dioxide); nabumetone (i.e., 4-(6-methoxy-2-naphthyl)-2-butanone); oxaprozin (i.e., 3-(4,5-diphenyl-1,3-oxazol-2-yl)propanoic acid); piroxicam (i.e., 4-hydroxy-2-methyl-N-2-pyridinyl-2H-1,2-benzothiazine-3-carboxamide 1,1-dioxide); salsalate (i.e., 2-(2-Hydroxybenzoyl)-oxybenzoic acid); sulindac (i.e., {(1Z)-5-fluoro-2-methyl-1-[4-(methylsulfinyl)-benzylidene]-1H-indene-3-yl}acetic acid); and tolmetin (i.e., [1-methyl-5-(4-methylbenzoyl)-1H-pyrrol-2-yl]acetic acid).

The NSAIDs include all pharmaceutically acceptable versions of the NSAIDs, including, for example, stereoisomers and/or any mixtures thereof, all pharmaceutically acceptable zwitterions and/or any mixtures thereof, all pharmaceutically acceptable polymorphic forms and/or any mixtures thereof, and all pharmaceutically acceptable complexes (including solvates) and/or any mixtures thereof.

NSAID salts include all salts of NSA IDs which are pharmaceutically acceptable (i.e., non-toxic at therapeutically effective doses). For example, NSAID salts include their racemates, enantiomers, or any mixtures thereof.

Particularly suitable salts of the NSAIDs comprise alkali-metal salts (e.g., sodium and/or potassium salts), alkaline earth metal salts (e.g., magnesium and/or calcium salts), aluminum salts, ammonium salts, salts of suitable organic bases (e.g., salts of alkylamines and/or -methyl-D-glutamine), salts of amino acids (e.g., salts of arginine and/or lysine). The NSAID salts also include all enantiomeric salts formed with pharmaceutically acceptable chiral acids and/or bases and/or any mixtures of enantiomers of such salts (e.g., (+) tartrates, (−) tartrates and/or any mixtures thereof including racemic mixtures). For example, a typical salt of an NSAID is naproxen sodium.

The $H_1$-antihistamines of the present invention include any $H_1$-antihistamine, preferably any non-sedating $H_1$-antihistamine. Examples of suitable $H_1$-antihistamines include, but are not limited to, loratadine (i.e., ethyl 4-(8-chloro-5,6-dihydro-11H-benzo[5,6]cyclohepta-[1,2-b]pyridin-11-ylidene)-1-piperidinecarboxylate); cetirizine (i.e., (±)-[2-[4-[(4-chlorophenyl)phenylmethyl]-1-piperazinyl]ethoxy] acetic acid); desloratadine (i.e., 8-chloro-6,11-dihydro-11-(4-piperdinylidene)-5H-benzo[5,6]cyclohepta[1,2-b] pyridine); and fexofenadine (i.e., (±)-4-[1 hydroxy-4-[4-(hydroxydiphenylmethyl)-1-piperidinyl]-butyl]-α,α-dimethyl benzeneacetic acid).

After intake of alcohol, many people develop symptoms referred to as "hangover" symptoms or veisalgia. These symptoms include, for example, substantial physical and mental fatigue, drowsiness, nausea, loss of appetite, tremors of the hand and limbs (the "shakes"), joint weakness/pain, dehydration, dry mouth (i.e., thirst), irritability, anxiety, lack of coordination, dizziness, difficulty in concentration, sleep disturbances (e.g., sleeplessness), impaired memory and visual-spatial skills, gastro-intestinal complaints, sweating and headache.

The methods of the present invention comprise the administration of the pharmaceutical composition to a human in an amount which is effective to inhibit the symptoms occurring after moderate or excessive alcohol intake.

It is surprising that the compositions of the present invention inhibit the symptoms of hangover. For example, the thirst (i.e., dry mouth) associated with alcohol consumption is believed to be caused by alcohol's inhibition of vasopressin, otherwise known as antidiuretic hormone (ADH). By inhibiting ADH, diuresis occurs. It is believed that this diuresis is responsible for the thirst associated with veisalgia. In addition, thirst is modulated from the hypothalamus, and alcohol may have an effect at the hypothalamus to cause thirst. NSAIDs are not known to affect ADH or have any effect on the hypothalamus, nor decrease thirst by any mechanism. Non-sedating anti-histamines are not known to affect ADH or affect the hypothalamus to any degree that could modulate thirst. For example, neither naproxen nor fexofenadine, alone, has shown any effect or side effect of reducing thirst. However, when taken in combination, prior to alcohol consumption, they have surprisingly been found to prevent, inhibit or reduce alcohol-induced thirst.

Typically, alcohol is ingested in the form of alcoholic beverages containing ethanol, and sometimes methanol. Also, alcoholic beverages can be inhaled directly into the respiratory system with aid of a vaporizing or nebulizing device for recreational use and/or absorbed through mucosal membranes, such as, e.g., through vaginal or rectal tissue.

A commonly used metric of alcohol intake is "blood alcohol content" (BAC), also called blood alcohol concentration, blood ethanol concentration, or blood alcohol level. Blood alcohol content is usually expressed as a percentage of ethanol in the blood in units of mass of alcohol per volume of blood or mass of alcohol per mass of blood, depending on the country. For instance, in North America a BAC of 0.1% (0.1% or one tenth of one percent) means that there is 0.10 g of alcohol for every dL of blood.

The methods of the present invention are effective for inhibiting one or more hangover symptom where the alcohol intake results in a BAC which can be considered moderate to excessive alcohol intake. For example, the methods are effective for alcohol intake that results in a BAC of from about 0.01% to about 0.3%. Examples of other lower boundaries of this range include about 0.03%, about 0.06%, about 0.09%, about 0.10% and about 0.12%. Examples of other upper boundaries of this range include about 0.15%, about 0.17%, about 0.19%, about 0.20% and about 0.25%.

In the present specification, the term "inhibit" includes "reduce" and/or "prevent" and/or "shorten duration." That is, the method of the present invention is considered to be effective if it causes one or more of: a reduction/inhibition/prevention of any symptom associated with veisalgia and/or shortening of the duration of an episode of any such symptom.

Reduction of symptoms can be assessed by comparing the magnitude and/or duration of at least one hangover symptom in a subject at two different occasions, that is, i) when administered the pharmaceutical composition, and then the subject intakes alcohol to attain a certain BAC; and ii) when not administered the pharmaceutical composition, and then the subject intakes alcohol to attain substantially the same BAC. Typically, hangover symptoms are reduced by at least about 10%, at least about 20%, at least about 30%, at least about 40%, at least about 50%, at least about 60%, at least about 70%, at least about 80%, at least about 90%, or at least about 100%.

For example, the method of the present invention is considered to be effective if it reduces/inhibits/prevents headache and/or fatigue and/or thirst, or shortens the duration of an episode of headache and/or fatigue and/or thirst. For instance, by the methods of the invention, reduction of the hangover symptoms of pain and fatigue were completely prevented or reduced by at least 60% or 80%, wherein the BAC was up to about 0.17; and reduction of the hangover symptom of thirst was completely prevented or reduced by at least about 75%, wherein the BAC ranged from about 0.05 to 0.1.

The actual preferred amounts of pharmaceutical composition in a specified case will vary according to the particular compositions formulated, the mode of application, the particular sites of application, and the subject being treated (e.g., age, gender, size, tolerance to drug, etc.).

Examples of typical amounts of NSAIDs to be administered in the methods of the present invention follows. Naproxen sodium from about 150 mg to about 900 mg: Examples of other lower boundaries of this range include about 220 mg, about 275 mg, about 320 mg and about 420 mg. Examples of other upper boundaries of this range include about 580 mg, about 680 mg, about 780 mg and about 880 mg. Other suitable amounts of naproxen include from about 110 mg to about 950 mg.

Ibuprofen from about 150 mg to about 900 mg: Examples of other lower boundaries of this range include about 200 mg, about 220 mg, about 320 mg and about 420 mg. Examples of other upper boundaries of this range include about 580 mg, about 680 mg, about 780 mg and about 800 mg. Other suitable amounts of ibuprofen include from about 100 mg to about 950 mg.

Aspirin from about 250 mg to about 1200 mg: Examples of other lower boundaries of this range include about 325 mg, about 450 mg, about 550 mg and about 650 mg. Examples of other upper boundaries of this range include about 750 mg, about 850 mg, about 950 mg, and about 1000 mg.

Examples of typical amounts of $H_1$-antihistamines to be administered in the methods of the present invention follows. Fexofenadine from about 25 mg to about 200 mg: Examples of other lower boundaries of this range include about 60 mg, about 70 mg, about 80 mg and about 90 mg. Examples of other upper boundaries of this range include about 95 mg, about 100 mg, about 110 mg and about 120 mg. Loratadine from about 5 mg to about 40 mg: Examples of other lower boundaries of this range include about 10 mg, about 12 mg and about 15 mg. Examples of other upper boundaries of this range include about 16 mg, about 18 mg and about 20 mg. Cetirizine from about 2 mg to about 40 mg: Examples of other lower boundaries of this range include about 5 mg, about 12 mg and about 15 mg. Examples of other upper boundaries of this range include about 16 mg, about 18 mg and about 20 mg. Desloratidine from about 2 mg to about 40 mg: Examples of other lower boundaries of this range include about 5 mg, about 6 mg and about 7 mg. Examples of other upper boundaries of this range include about 8 mg, about 9 mg and about 10 mg.

In the methods of the present invention, the pharmaceutical composition is administered before the onset of symptoms. For example, administration is at most about 120 minutes before alcohol intake, at most about 90 minutes before alcohol intake, at most about 60 minutes before alcohol intake, at most about 30 minutes before alcohol intake, at most about 20 minutes before alcohol intake, just right before the alcohol intake, or simultaneously with alcohol intake. In some embodiments, the pharmaceutical composition can be administered up to about 2 hours to about 4 hours after alcohol intake, but before the onset of symptoms. Hangover symptoms typically develop when BAC begins to decline, typically when BAC returns to substantially about zero.

The pharmaceutical composition can be administered by methods known in the art. For example, the pharmaceutical composition can be administered systemically. For the purposes of this specification, "systemic administration" means administration to a human by a method that causes the compositions to be absorbed into the bloodstream.

In one embodiment, the pharmaceutical compositions are administered orally by any method known in the art. For example, the compositions can be administered in the form of tablets, including, e.g., orally-dissolvable tablets, chewable tablets; capsules; lozenges; pills (e.g., pastilles, dragees); troches; elixirs; suspensions; syrups; wafers; chewing gum; strips; films (e.g., orally-dissolving thin films); soluble powders; effervescent compositions; and the like.

The NSAID (and/or salt thereof) and the $H_1$-antihistamine can be supplied in combination as one unit dose, or can be supplied individually, e.g., supplied in a package with a unit dose of NSAID and a unit dose of $H_1$-antihistamine.

Additionally, the pharmaceutical compositions can be administered enterally or parenterally, e.g., intravenously; intramuscularly; subcutaneously, as injectable solutions or suspensions; intraperitoneally; sublingually; or rectally (e.g., by suppositories). Administration can also be intranasally, in the form of, for example, an intranasal spray; or transdermally, in the form of, for example, a patch.

The pharmaceutical composition compounds of the invention can be formulated per se in pharmaceutical preparations, optionally, with a suitable pharmaceutical carrier (vehicle) or excipient, as understood by practitioners in the art. These preparations can be made according to conventional chemical methods.

In the case of tablets for oral use, carriers commonly used include lactose and corn starch, and lubricating agents such as magnesium stearate are commonly added. For oral administration in capsule form, useful carriers include lactose and corn starch. Further examples of carriers and excipients include milk, sugar, certain types of clay, gelatin, stearic acid or salts thereof, calcium stearate, talc, vegetable fats or oils, gums and glycols.

When aqueous suspensions are used for oral administration, emulsifying and/or suspending agents are commonly added. In addition, sweetening and/or flavoring agents may be added to the oral compositions.

For intramuscular, intraperitoneal, subcutaneous and intravenous use, sterile solutions of the pharmaceutically compositions can be employed, and the pH of the solutions can be suitably adjusted and buffered. For intravenous use, the total concentration of the solute(s) can be controlled in order to render the preparation isotonic.

A preferred embodiment of the invention is an orally dissolving tablet comprising an NSAID and a non-sedating antihistamine with or without a taste masking ingredient, diluents, etc. Such tablet can be administered without water onto the tongue leading to immediate dissolution and is absorbed gastrointestinally or buccally. Orally dissolving tablets can be formulated by a number of techniques including compression and lyophilization, as would be known to a skilled artisan.

Another preferred embodiment of the invention is a lozenge or troche comprising an NSAID and a non-sedating antihistamine with or without a taste masking ingredient, diluents, etc. Such lozenge/troche can be administered without water, and can slowly dissolve in the mouth, or can be swallowed or chewed. Such lozenges/troches can be formulated by compression, as would be known to a skilled artisan.

The pharmaceutical compositions of the present invention can further comprise one or more pharmaceutically acceptable additional ingredient(s) such as alum, stabilizers, buffers, coloring agents, flavoring agents, and the like. In some embodiments, orally administered pharmaceutical compositions can contain breathe neutralizers, e.g., peppermint or menthol scents.

In some embodiments, the pharmaceutical compositions can include further active ingredients. Examples of such active ingredients include a proton pump inhibitor and an H-2 antagonist.

The pharmaceutical composition may be administered by controlled release. Controlled release administration is a method of drug delivery to achieve a certain level of the drug over a particular period of time. The level typically is measured by plasma concentration. Methods for controlled release of drugs are well known in the art.

The pharmaceutical compositions can be formulated for controlled release. For example, in one embodiment, the composition can be a capsule containing beadlets, wherein some of the beadlets dissolve instantaneously and some of the beadlets dissolve at delayed times due to different types of beadlet coatings.

In one embodiment, the pharmaceutical composition comprises an active ingredient, wherein the active ingredient consists of: a) NSAID, and/or salt thereof, and b) $H_1$-antihistamine.

In one embodiment, the pharmaceutical composition consists of: a) NSAID, and/or salt thereof, b) $H_1$-antihistamine, and c) at least one carrier and/or excipient.

In one embodiment, the pharmaceutical composition consists essentially of the active ingredients of: a) NSAID and/or salt thereof, and b) $H_1$-antihistamine. That is, any other ingredients that may materially affect the basic and novel characteristics of the active ingredients of the invention are specifically excluded from the composition. Any ingredient which can potentially cause an undesirable effect/side effect, including, for example, an allergic response, may materially affect the basic and novel characteristics of the active ingredients of the invention.

The following are some examples of components which may materially affect the basic and novel characteristics of the active ingredients of the pharmaceutical compositions and may be excluded from certain embodiments of the present invention: decongestants, sedating antihistamines, nicotinamide; NAD; agonists of cannabinoid receptors; N-benzyl pyrrole compounds; an anti-CGRP antibody/antibody fragment or a polypeptide comprising such fragments; 4-methylpyrazole or salt thereof; and/or ginsenoside.

The aforementioned ingredients may materially change the characteristics of the present pharmaceutical composition due to unwanted effects and/or potential allergic responses. For example, decongestant and/or sedating effects are not desired in some embodiments of the invention. Examples of unwanted potential effects of nicotinamide and NAD include upset stomach, nausea, vomiting, diarrhea, black/tarry stools, easy bruising/bleeding, edema, and jaundice. Examples of unwanted potential effects of agonists of cannabinoid receptors include difficulties with short-term memory, agitation, feeling tense, anxiety, dizziness or lightheadedness, confusion, and loss of coordination, episodes of psychosis and panic. Examples of unwanted potential effects of N-benzyl pyrrole compounds include allergic responses. Examples of unwanted potential effects of anti-CGRP antibody/antibody fragments include allergic reactions, fever and vomiting. Examples of unwanted potential effects of 4-methylpyrazole include elevation of serum transaminase values. Examples of unwanted potential effects of ginsenoside include hormone-like effects (e.g., menstrual problems, breast pain, vaginal bleeding), insomnia, increased heart rate, blood pressure variations, headache, diarrhea, itching, rash, dizziness, mood changes.

In one embodiment, the pharmaceutical formulation does not comprise decongestants, sedating antihistamines, nicotinamide; nicotinamide adenine dinucleotide (NAD); agonists of cannabinoid receptors; N-benzyl pyrrole compounds; an anti-CGRP antibody/antibody fragment, or a polypeptide comprising such fragment; 4-methylpyrazole or salt thereof; and ginsenoside.

EXAMPLES

The following examples demonstrate that the hangover symptoms of headache and fatigue are reduced or prevented when using the methods of the present invention. Headache pain was measured using a visual analog pain scale 0-10, where 10 is the highest level of pain. Fatigue was measured using a visual analog fatigue scale 0-10, where 10 is the most fatigued.

Example #1

58 year old female weighing approximately 120 pounds, in good health, and taking no medications, ingested naproxen sodium 220 mg and fexofenadine 60 mg just prior to drinking. She drank 5 glasses of white wine (5 oz each) over the course of 4 hours. This correlates to a blood alcohol concentration of approximately 0.13%. Drinks were consumed throughout dinner and after dinner followed by sleep. Headache pain the next morning/day using the visual analog pain scale was reported to be 1. Fatigue the next morning/day using the visual analog fatigue scale was reported to be 0.

After a thorough washout period, and without taking any medications prior to drinking, the subject drank 4.5 glasses of white wine (5 oz each) over the course of 5 hours. This correlates to a blood alcohol concentration of approximately 0.10%. Drinks were consumed throughout dinner and after dinner, followed by sleep. Headache pain the next morning/day using the visual analog pain scale was reported to be 8. Fatigue the next morning/day using the visual analog fatigue scale was reported to be 4.

Example #2

54 year old female weighing approximately 130 pounds, in good health, taking no medications, ingested naproxen sodium 220 mg and fexofenadine 60 mg just prior to drinking. She drank 3 glasses of red wine (5 oz each) over 3.5 hours. This correlates to a blood alcohol concentration of approximately 0.07%. Drinks were consumed during dinner and after dinner, followed by sleep. Headache pain the next morning/day using the visual analog pain was reported to be 0. Fatigue the next morning/day using the visual analog fatigue scale was reported to be 2.

After a 4 day washout period, the subject ingested naproxen sodium 220 mg and fexofenadine 60 mg just prior to drinking. She drank 3 glasses of beer (12 oz each) with 8-10% alcohol content over 2 hours. This correlates to a blood alcohol concentration of approximately 0.09%. Drinks were consumed during and after dinner, followed by sleep. Headache pain the next morning/day using the visual analog pain scale was reported to be 3. Fatigue the next morning/day using the visual analog fatigue scale was reported to be 0.

After a thorough washout period, and without taking any medication prior to drinking, the subject drank 5 glasses of white wine (5oz each) over 3.5 hours. This correlates to a blood alcohol concentration of approximately 0.11%. Drinks were consumed during and after dinner, followed by sleep. Headache pain the next morning/day using the visual analog pain scale was reported to be 4. Fatigue the next morning/day using the visual analog fatigue scale was reported to be 5.

After a thorough washout period, the subject ingested naproxen sodium 220 mg and fexofenadine 60 mg just prior to drinking. She drank 3 glasses of beer (12 oz each) over 2.5 hours. This correlates to a blood alcohol concentration of approximately 0.07%. Drinks were consumed during and after dinner, followed by sleep. Headache pain the next morning/day using the visual analog pain scale was reported to be 0. Fatigue the next morning/day using the visual analog fatigue scale was reported to be 0.

After a thorough washout period, and without taking any medication prior to drinking, the subject drank 3 beers (12 oz each), 1 tequila (1.25 oz), and red wine (5 oz) over 3 hours. This correlates to a blood alcohol concentration of approximately 0.11%. Drinks were consumed during and after dinner, followed by sleep. Headache pain the next morning/day using the visual analog pain scale was reported to be 7. Fatigue the next morning/day using the visual analog fatigue scale was reported to be 9.

After a thorough washout period, the subject ingested naproxen sodium 220 mg and fexofenadine 60 mg just prior to drinking. She drank 3 glasses of beer (12 oz each) over 2 hours. This correlates to a blood alcohol concentration of approximately 0.09%. Drinks were consumed during and after dinner, followed by sleep. Headache pain the next morning/day using the visual analog pain scale was reported to be 0. Fatigue the next morning/day using the visual analog fatigue scale was reported to be a 3.

Example #3

52 year old female, weighing 120 pounds, in good health, on hormone replacement therapy ingested naproxen sodium 220 mg and fexofenadine 60 mg just prior to drinking. She drank 1 glass of white wine and 2 glasses of red wine (5 oz each) over 2.5 hours. This correlates to a blood alcohol concentration of approximately 0.07%. Drinks were consumed during and after dinner, followed by sleep. Headache pain the next morning/day using the visual analog pain scale was reported to be 1. Fatigue the next morning/day using the visual analog fatigue scale was reported to be 1.

After a thorough washout period, and without taking any medication prior to drinking, the subject drank 1 glass of white wine and 1 glass of red wine (5 oz each) over 2 hours. This correlates to a blood alcohol concentration of approximately 0.05%. Drinks were consumed during and after dinner, followed by sleep. Headache pain the next morning/day using the visual analog pain scale was reported to be 4. Fatigue the next morning/day using the visual analog fatigue scale was reported to be 3.

After a thorough washout period, the subject ingested naproxen sodium 220 mg and fexofenadine 60 mg just prior to drinking. She drank 1 glass of white wine and 2 glasses of red wine (5 oz each) over 2 hours. This correlates to a blood alcohol concentration of approximately 0.08%. Drinks were consumed during and after dinner, followed by sleep. Headache pain the next morning/day using the visual analog pain scale was reported to be 1. Fatigue the next morning/day using the visual analog fatigue scale was reported to be 1.

After a thorough washout period, and without taking any medication prior to drinking, the subject drank 1 glass of white wine (5 oz) and 2 glass of red wine (5 oz each) over 2 hours. This correlates to a blood alcohol concentration of approximately 0.08%. Drinks were consumed during and after dinner, followed by sleep. Headache pain the next morning/day using the visual analog pain scale was reported to be 6. Fatigue the next morning/day using the visual analog fatigue scale was reported to be 4.

After a thorough washout period, the subject ingested naproxen sodium 220 mg and fexofenadine 60 mg just prior to drinking. She drank tequila (1.25 oz), 1 glass white wine (5 oz) and 4 glasses red wine (5 oz each) over 4 hours. This correlates to a blood alcohol concentration of approximately 0.17%. Drinks were consumed during and after dinner, followed by sleep. Headache pain the next morning/day using the visual analog pain scale was reported to be 0. Fatigue the next morning/day using the visual analog fatigue scale was reported to be 1.

After a thorough washout period, and without taking any medication prior to drinking, the subject drank 2 glasses of white wine (5 oz each) and 4 glasses of red wine (5 oz each) over 4 hours. This correlates to a blood alcohol concentration of approximately 0.17%. Drinks were consumed during and after dinner, followed by sleep. Headache pain the next morning/day using the visual analog pain scale was reported to be 8. Fatigue the next morning/day using the visual analog fatigue scale was reported to be 7.

Example #4

52 year old male, 220 pounds, in good health, on losarten for blood pressure, ingested naproxen sodium 220 mg and fexofenadine 60 mg just prior to drinking. He drank 2 vodka drinks (2.5 oz each) on the rocks, 3 glasses red wine (5 oz each) over 2.5 hours. This correlates to a blood alcohol concentration of approximately 0.08%. Drinks were consumed during and after dinner, followed by sleep. Headache pain the next morning/day using the visual analog pain scale was reported to be 0. Fatigue the next morning/day using the visual analog fatigue scale was reported to be 0.

After a thorough washout period, and without taking any medication prior to drinking, the subject drank 2 vodka drinks (2.5 oz each) on the rocks, 3 glasses of red wine (5 oz each) over 2.5 hours. This correlates to a blood alcohol concentration of approximately 0.08%. Drinks were consumed during and after dinner, followed by sleep. Headache pain the next morning/day using the visual analog pain scale was reported to be 5. Fatigue the next morning/day using the visual analog fatigue scale was reported to be 7.

After a thorough washout period, the subject ingested naproxen sodium 220 mg and fexofenadine 60 mg just prior to drinking. He drank 2 vodka drinks (2.5 oz each) on the rocks, 2 glasses red wine (5 oz each) over 2.5 hours. This correlates to a blood alcohol concentration of approximately 0.06%. Drinks were consumed during and after dinner, followed by sleep. Headache pain the next morning/day using the visual analog pain scale was reported to be 0. Fatigue the next morning/day using the visual analog fatigue scale was reported to be 0.

After a thorough washout period, and without taking any medication prior to drinking, the subject drank 2 vodka drinks (2.5 oz each) on the rocks, 2 glasses of red wine (5 oz each) over 2.5 hours. This correlates to a blood alcohol concentration of approximately 0.06%. Drinks were consumed during and after dinner, followed by sleep. Headache pain the next morning/day using the visual analog pain scale was reported to be 5. Fatigue the next morning/day using the visual analog fatigue scale was reported to be 7.

The following table summarizes the results of the foregoing Examples.

| Example | | Pain | Fatigue | Est. BAC |
|---|---|---|---|---|
| #1 | No-Drug | 8 | 4 | 0.10% |
|    | Drug    | 1 | 0 | 0.13% |
| #2 | No-Drug | 4 | 5 | 0.11% |
|    | No-Drug | 7 | 9 | 0.11% |
|    | Drug    | 3 | 0 | 0.09% |
|    | Drug    | 0 | 3 | 0.09% |
| #3 | No-Drug | 4 | 3 | 0.05% |
|    | No-Drug | 6 | 4 | 0.08% |
|    | No-Drug | 8 | 7 | 0.17% |
|    | Drug    | 1 | 1 | 0.07% |
|    | Drug    | 1 | 1 | 0.08% |
|    | Drug    | 0 | 1 | 0.17% |
| #4 | No-Drug | 5 | 7 | 0.08% |
|    | No-Drug | 5 | 7 | 0.06% |
|    | Drug    | 0 | 0 | 0.08% |
|    | Drug    | 0 | 0 | 0.06% |

Note:
Using Scale 0-10 for both Pain & Fatigue.
Mean +/− Standard Deviation
Pain: No-Drug = 5.80 +/− 1.64
      Drug = 0.75 +/− 1.03
Fatigue: No-Drug = 5.75 +/− 1.64
         Drug = 0.75 +/− 1.03

The following examples demonstrate the prevention or reduction of the hangover symptom of thirst when using the methods/compositions of the present invention.

Each volunteer subject was tested on two separate occasions. On one occasion, a subject was administered the drug combination of naproxen 220 mg and fexofenadine 60 mg prior to moderate alcohol consumption. On another occasion, the subject consumed substantially the same amount and type of alcohol, but was not administered the drug.

The thirst of the subjects was measured the day after alcohol consumption, during the time period typically associated with hangover like symptoms. Thirst was measured using a 0-7 scale, where 0=no thirst, 4=moderate thirst, and 7=incapacitating thirst. The results follow below.

Example #5

58 year old female, approximately 120 pounds
Thirst level when no drug administered=5, BAC=0.05%
Thirst level when drug administered=1, BAC=0.09%

Example #6

54 year old female, approximately 130 pounds
Thirst level when no drug administered=4, BAC=0.07%
Thirst level when drug administered=0, BAC=0.07%

Example #7

52 year old female approximately 120 pounds
Thirst level when no drug administered=4, BAC=0.10%
Thirst level when drug administered=1, BAC=0.10%

Example #8

52 year old male, approximately 220 pounds
Thirst level when no drug administered=5, BAC=0.08%
Thirst level when drug administered=1, BAC=0.08%
Summary of Results Evaluating Thirst
Without Drug: Mean+/−SD=4.5+/−0.5
With Drug: Mean+/−SD=0.75+/−0.5

Thus, while there have been described what are presently believed to be the preferred embodiments of the present invention, other and further embodiments, modifications, and improvements will be known to those skilled in the art, and it is intended to include all such further embodiments, modifications, and improvements as come within the true scope of the claims as set forth below.

The invention claimed is:

1. A method of inhibiting the symptoms associated with intake of alcohol, consisting of:
   administering to a subject an effective amount of a pharmaceutical composition prior to alcohol intake, wherein the pharmaceutical composition consists of:
   a) a non-steroidal anti-inflammatory drug selected from the group consisting of naproxen, a salt of naproxen, ibuprofen, and a salt of ibuprofen;
   b) an $H_1$-antihistamine selected from the group consisting of fexofenadine and cetirizine, and
   c) optionally, a pharmaceutical carrier, a pharmaceutical excipient, a sweetening agent, a flavoring agent, a taste masking ingredient, a diluent, alum, a stabilizer, a buffer, a coloring agent, a breath neutralizer, a proton pump inhibitor, an emulsifying agent, a suspending agent, and combinations thereof,
   wherein the symptoms associated with the intake of alcohol are inhibited.

2. The method of claim 1 wherein the alcohol is ethanol in the form of beverages.

3. The method of claim 1 wherein the non-steroidal anti-inflammatory drug is naproxen sodium and the $H_1$-antihistamine is fexofenadine.

4. The method of claim 3 wherein the amount of naproxen sodium is about 220 mg to about 880 mg, and the amount of fexofenadine is about 60 mg to about 120 mg.

5. The method of claim 4 wherein the naproxen sodium and the fexofenadine are combined in one unit dose.

6. The method of claim 4 wherein the naproxen sodium and the fexofenadine are in the form of a tablet, lozenge or chewing gum.

7. The method of claim 1 wherein the excessive intake of alcohol is an amount which provides a blood alcohol concentration of up to about 0.17%.

8. The method of claim 1 wherein the pharmaceutical composition is administered at most 60 minutes before intake of alcohol.

9. The method of claim 1 wherein the pharmaceutical composition is administered at most 5 minutes before intake of alcohol.

10. The method of claim 1 wherein the symptoms include fatigue and/or headache.

11. The method of claim 1 wherein the amount of ibuprofen is about 200 mg to about 800 mg.

12. The method of claim 1 wherein the amount of cetirizine is about 5 mg to about 20 mg.

13. The method of claim 1 wherein the symptoms include thirst.

14. A method of inhibiting the symptoms associated with intake of alcohol, consisting of:
    administering to a subject an effective amount of a pharmaceutical composition prior to alcohol intake, wherein the pharmaceutical composition consists of:
    a) about 220 mg to about 880 mg of naproxen sodium, and about 60 mg to about 120 mg fexofenadine, and
    b) optionally, a pharmaceutical carrier, a pharmaceutical excipient, a sweetening agent, a flavoring agent, a taste masking ingredient, a diluent, alum, a stabilizer, a buffer, a coloring agent, a breath neutralizer, a proton pump inhibitor, an emulsifying agent, a suspending agent, and combinations thereof,
    wherein the symptoms associated with the intake of alcohol are inhibited.

15. A method of inhibiting the symptoms associated with intake of alcohol, consisting of:
    administering to a subject an effective amount of a pharmaceutical composition prior to alcohol intake, wherein the pharmaceutical composition consists of:
    a) naproxen, and/or a salt thereof; and b) fexofenadine, and c) optionally, a pharmaceutical carrier, a pharmaceutical excipient, a sweetening agent, a flavoring agent, a taste masking ingredient, a diluent, alum, a stabilizer, a buffer, a coloring agent, a breath neutralizer, a proton pump inhibitor, an emulsifying agent, a suspending agent, and combinations thereof,
    wherein the symptoms associated with the intake of alcohol are inhibited.

* * * * *

UNITED STATES PATENT AND TRADEMARK OFFICE
CERTIFICATE OF CORRECTION

| | | |
|---|---|---|
| PATENT NO. | : 10,420,756 B2 | Page 1 of 1 |
| APPLICATION NO. | : 15/074524 | |
| DATED | : September 24, 2019 | |
| INVENTOR(S) | : Iversen et al. | |

It is certified that error appears in the above-identified patent and that said Letters Patent is hereby corrected as shown below:

In the Specification

<u>Column 1, Line 6</u>:
Delete: "Application Ser. No. 61/138,665"
Insert: -- Application Ser. No. 62/138,665 --

Signed and Sealed this
Twenty-fourth Day of March, 2020

Andrei Iancu
*Director of the United States Patent and Trademark Office*